United States Patent [19]

Klaveness

[11] Patent Number: 5,242,683
[45] Date of Patent: Sep. 7, 1993

[54] CONTRAST MEDIA COMPRISING A PARAMAGNETIC AGENT AND AN IODINATED AGENT FOR X-RAY AND MRI

[75] Inventor: Jo Klaveness, Oslo, Norway
[73] Assignee: Nycomed Imaging AS, Oslo, Norway
[21] Appl. No.: 778,054
[22] PCT Filed: Jul. 19, 1990
[86] PCT No.: PCT/EP90/01197
§ 371 Date: Dec. 10, 1991
§ 102(e) Date: Dec. 10, 1991
[87] PCT Pub. No.: WO91/01149
PCT Pub. Date: Feb. 7, 1991

[30] Foreign Application Priority Data

Jul. 21, 1989 [GB] United Kingdom ............. 8916781

[51] Int. Cl.$^5$ ............. G01N 24/08; G01N 23/04; A61K 31/555
[52] U.S. Cl. ............. 424/9; 424/4; 424/5; 436/173; 436/806; 128/653.4; 514/184; 514/492; 514/836; 534/16
[58] Field of Search ............. 424/4, 5, 9; 436/173, 436/806; 128/653.4, 654; 514/836, 184, 492; 534/16

[56] References Cited

U.S. PATENT DOCUMENTS

| | | | |
|---|---|---|---|
| 2,387,735 | 10/1945 | Bersworth | 260/534 |
| 2,407,645 | 9/1946 | Bersworth | 260/534 |
| 4,615,879 | 10/1986 | Runge et al. | 424/9 |
| 4,639,365 | 1/1987 | Sherry | 424/9 |
| 4,647,447 | 3/1987 | Gries et al. | 424/9 |
| 4,714,607 | 12/1987 | Klaveness | 424/9 |
| 4,719,098 | 1/1988 | Weinmann et al. | 424/9 |
| 4,760,173 | 7/1988 | Klaveness | 562/449 |
| 4,826,673 | 5/1989 | Dean et al. | 424/9 |
| 4,880,008 | 11/1989 | Lauffer | 128/653.4 |
| 4,885,363 | 12/1989 | Tweedle et al. | 540/465 |
| 4,916,170 | 4/1990 | Nambu et al. | 523/137 |
| 4,980,502 | 12/1990 | Felder et al. | 562/444 |
| 5,013,831 | 5/1991 | Stavrianopoulos | 536/27 |
| 5,082,928 | 1/1992 | Best | 530/389 |
| 5,104,641 | 4/1992 | Rosen | 424/9 |
| 5,114,703 | 5/1992 | Wolf et al. | 424/5 |

FOREIGN PATENT DOCUMENTS

| | | |
|---|---|---|
| 78995/87 | 3/1988 | Australia . |
| 10649/88 | 7/1988 | Australia . |
| 1253514 | 5/1989 | Canada . |
| 0165728 | 12/1985 | European Pat. Off. . |
| 0184899 | 6/1986 | European Pat. Off. . |
| 0186947 | 7/1986 | European Pat. Off. . |
| 0258616 | 3/1988 | European Pat. Off. . |
| 0284549 | 9/1988 | European Pat. Off. . |
| 0299795 | 1/1989 | European Pat. Off. . |

OTHER PUBLICATIONS

Kornmesser et al., *Fortschr. Rontgenstr.*, 147, 5, 550–556 (1987).
Laniado et al., *Enhanced Magnetic Resonance Imaging*, 1989.
Wolf et al., *Chemical Abstracts*, 101:14734j, 1984.
Aime et al., *Chemical Abstracts*, 110:91376f, 1989.
Lauterbur et al., *Frontiers of Biological Energetics*, 1, 752–759 (1984).
Laniado et al., *Fortschr. Rontgenstr.*, 147, 325–332, 1987 (abstract only).
Claussen et al., *Fortschr. Rontenstr.*, 148, 683–689, 1988 (Abstract only).

*Primary Examiner*—Allen J. Robinson
*Assistant Examiner*—Gary E. Hollinden
*Attorney, Agent, or Firm*—Bacon & Thomas

[57] ABSTRACT

There is provided a contrast medium comprising a physiologically tolerable paramagnetic metal species containing substance together with a water soluble iodinated X-ray contrast agent. The contrast medium can be used for both X-ray and magnetic resonance imaging of the gastro-intestinal tract but overcomes or greatly reduces the side effects experienced by mannitol-containing prior art contrast media.

20 Claims, No Drawings

CONTRAST MEDIA COMPRISING A PARAMAGNETIC AGENT AND AN IODINATED AGENT FOR X-RAY AND MRI

The present invention relates to improvements in and relating to contrast media for use in diagnostic imaging, and especially to contrast media suitable for imaging the gastrointestinal (GI) tract.

In X-ray imaging and magnetic resonance imaging (MRI), contrast agents may be administered to the patient in order to enhance image contrast between regions into which the contrast agent distributes and those into which it does not, or between regions into which the contrast agent distributes unequally.

For X-ray imaging, the contrast agents comprise relatively high atomic number atoms, e.g. barium or iodine, as X-ray transmission generally decreases as atomic number increases. For MR imaging however, the contrast agents are generally substances which affect the nuclear spin reequilibration of the nuclei (hereinafter the "imaging nuclei"—generally water protons in body tissues and fluids) which are responsible for the MR signals from which MR images are generated.

Accordingly, in recent years, many such substances have been suggested for use as MRI contrast agents. Thus, for example, in 1978 Lauterbur proposed the use of paramagnetic species, such as Mn(II), as MRI contrast agents (see Lauterbur et al., pages 752–759 in "Electrons to Tissues—Frontiers of Biologic Energetics", Volume 1, edited by Dutton et al., Academic Press, New York, 1978) and more recently Schering AG, in EP-A-71564, proposed the use of the dimeglumine salt of the gadolinium(III) chelate of diethylenetriaminepentaacetic acid (GdDTPA-dimeglumine).

Many other paramagnetic MRI contrast agents have been suggested in the literature and in this regard reference may be had to EP-A-71564 (Schering), EP-A-130934 (Schering), U.S. Pat. No. 4,615,879 (Runge), DE-A-3401052 (Schering), EP-A-185899 (Nycomed), EP-A-186947 (Nycomed), US. Pat. Nos. 2,387,735 (Bersworth), 2,407,645 (Bersworth), EP-A-165728 (Nycomed), U.S. Pat. Nos. 4,647,447 (Schering), 4,826,673 (Mallinckrodt), 4,639,365 (Sherry), EP-A-299795 (Nycomed), DE-A-2918842 (Rexolin Chemicals AB), EP-A-258616 (Salutar), DE-A-3633245 (Schering), EP-A-263059 (Schering), EP-A-277088 (Schering) and DE-A-3633243 (IDF) and in the documents cited in these patent publications.

Particularly interesting MRI contrast agents thus include chelates of paramagnetic metal species, e.g. Gd(III), Mn(II), Cr(III), Dy(III) and Fe(III) with cyclic or acyclic polyaminocarboxylic acids such as DOTA, DTPA, DTPA-bismethylamide, DTPA-bismorpholide, D03A, HP-D03A and derivatives thereof.

While MRI has until now mainly been used for imaging the central nervous system, the technique has great potential for imaging externally voided body cavities and especially the GI tract. However, development of MRI as a technique for imaging the GI tract, or indeed the abdomen in general, has been hindered by the special problems of imaging the abdomen in which, in the absence of a contrast agent, inter-tissue contrast is relatively poor and there is thus a general need for improved MRI contrast media suitable for imaging such body cavities.

Various substances have been evaluated as potential MRI contrast agents for the GI system, including for example paramagnetic compounds such as GdDTPA and GdDTPA-containing products are now in clinical trials as oral MRI contrast media (see for example Laniado et al. Fortschr. Röntgenstr. 147: 325–332 (1987), Kornmesser at al. Fortschr. Röntgenstr. 147: 550–556 (1987), Claussen et al. Fortschr. Röntgenstr. 148: 683–689 (1988), Laniado et al., Chapter 23 in "Enhanced Magnetic Resonance Imaging", edited by Runge, St Louis, 1989, and EP-124766 (Schering AG).

Paramagnetic substances have a relatively close range effect on the imaging nuclei and thus, to be effective as positive contrast agents, need to be in close proximity (at the molecular level) to water molecules. During passage through the GI system however water is absorbed and as result the contrast efficiency of paramagnetic MRI contrast media administered into the GI tract is reduced.

This problem has been addressed by Schering by the inclusion of mannitol within their GdDTPA-dimeglumine containing oral MRI contrast medium.

Schering (EP-A-124766), Claussen et al., Kornmesser et al. and Laniado et al. (1989) (supra) thus report results for oral MRI contrast media containing 0.5 or 1.0 mmol/l GdDTPA and 0, 15 and 30 g/l mannitol. Without mannitol homogeneous contrast enhancement in the entire small bowel was observed with only 2 of 5 subjects, this was increased to 4 of 5 with 15 g/l mannitol and to 5 of 5 with 30 g/l mannitol.

The addition of mannitol, however, resulted in side effects for the patients and even with only 15 g/l 13 out of 32 patients suffered meteorism and diarrhoea according to the results presented by Claussen et al. (supra).

We have surprisingly found that paramagnetic MRI contrast agents may be formulated with iodinated X-ray contrast agents to produce a contrast medium which can be used for imaging the GI tract by X-ray and/or MR imaging and which overcomes or substantially reduces the side effects of the prior art mannitol containing oral MRI contrast media referred to above.

In one aspect, therefore, the invention provides a contrast medium comprising a physiologically acceptable paramagnetic metal species containing substance together with a water soluble iodinated X-ray contrast agent.

The contrast media of the invention can, as mentioned above, be used for both X-ray and MR imaging of the GI tract. This makes such media particularly attractive for use in the examination of infants and elderly patients, patients with problems swallowing and, most especially, patients with powerful acute pain in the abdominal region, i.e. so-called "acute abdomen".

With such patients, it will be particularly advantageous to perform both MRI and X-ray imaging after the administration of only a single contrast agent, especially since relatively large volumes, e.g. 300–1000 ml, of contrast medium generally have to be administered in routine X-ray or MR imaging of the abdomen. Accordingly, use of a combined MR/X-ray imaging contrast medium will save both time and discomfort for the patient.

Since the contrast media of the invention incorporate paramagnetic metal species, and since such metals have medium to high atomic weights, the efficiency of the media of the invention as X-ray contrast media is enhanced by the inclusion of the paramagnetic substance. On the other hand, the efficiency of the media as MRI contrast media is not only increased by inclusion of the iodinated X-ray contrast agent but this is achieved without incurring or with a significantly reduced occurrence of the drawbacks that resulted from the use of mannitol.

The X-ray contrast agent in the media of the invention can be any iodinated, ionic or non-ionic water-soluble X-ray contrast agent, for example non-ionic monomers, ionic monomers, non-ionic dimers and ionic dimers. Such monomers or dimers generally contain within their molecular structure one or two triiodophenyl moieties respectively. Suitable examples include salts, e.g. sodium or meglumine salts, of iodamide, iothalamate, diatrizoate, ioxaglate and metrizoate, and non-ionics such as metrizamide (see DE-A-2031724), iopamidol (see BE-A-836355), iohexol (see GB-A-1548594), iotrolan (see EP-A-33426), iodecimol (see EP-A-49745), iodixanol (see EP-A-108638), ioglucol (see U.S. Pat. No. 4,314,055), ioglucomide (see BE-A-846657), ioglunioe (see DE-A-2456685), iogulamide (see BE-A-882309), iomeprol (see EP-A-26281), iopentol (see EP-A-105752), iopromide (see DE-A-2909439), iosarcol (see DE-A-3407473), iosimide (see DE-A-3001292), iotasul (see EP-A-22056), iovarsol (see EP-A-83964) and ioxilan (see WO87/00757).

Where the X-ray contrast agent is in salt form, the counterion should, of course, be physiologically acceptable and in this regard mention may be made of alkali and alkaline earth metal cations, e.g. sodium and calcium, and cations of organic bases such as ethanolamine, diethanolamine, morpholine, glucamine and especially meglumine.

Particular ionic X-ray contrast agents useful according to the invention thus include physiologically acceptable salts of 3-acetylamino-2,4-6-triiodobenzoic acid, 3,5-diacetamido-2,4,6-triiodobenzoic acid, 2,4,6-triiodo-3,5-dipropionamido-benzoic acid, 3-acetylamino-5-((acetylamino)methyl)-2,4,6-triiodobenzoic acid, 3-acetylamino-5-(acetylmethylamino)-2,4,6-triiodobenzoic acid, 5-acetamido-2,4,6-triiodo-N-((methylcarbamoyl)methyl)-isophthalamic acid, 5-(2-methoxyacetamido)-2,4,6-triiodo-N-[2-hydroxy-1-(methylcarbamoyl)-ethyl]-isophthalamic acid, 5-acetamido-2,4,6-triiodo-N-methylisophthalamic acid, 5-acetamido-2,4,6-triiodo-N-(2-hydroxyethyl)-isophthalamic acid, 2-[[2,4,6-triiodo-3[(1-oxobutyl)-amino]-triiodophenyl)-alpha-ethyl-propanoic phenyl]methyl]-butanoic acid, beta-(3-amino-2,4,6-acid, 3-ethyl-3-hydroxy-2,4,6-triiodophenyl-propanoic acid, 3-[[(dimethylamino)-methyl]amino]-2,4,6-triiodophenyl-propanoic acid (see Chem. Ber. 93: 2347 (1960)); alpha-ethyl-(2,4,6-triiodo-3-(2-oxo-1-pyrrolidinyl)-phenyl)-propanoic acid, 2-[2-[3-(acetylamino)-2,4,6-triiodophenoxy]ethoxymethyl]-butanoic acid, N-(3-amino-2,4,6-triiodobenzoyl)-N-phenyl-β-aminopropanoic acid, 3-acetyl-[(3-amino-2,4,6-triiodophenyl) amino]-2-methylpropanoic acid, 5-[(3-amino-2,4,6-triiodophenyl)methylamino]-5-oxypentanoic acid, 4-[ethyl-[2,4,6-triiodo 3-(methylamino)-phenyl]amino]-4-oxo-butanoic acid, 3,3'-oxybis[2,1-ethanediyloxy-(1-oxo-2,1-ethanediyl)imino]bis-2,4,6-triiodobenzoic acid, 4,7,10,13-tetraoxahexadecane-1,16-dioyl-bis(3-carboxy-2,4,6-triiodoanilide, 5,5'-(azelaoyl-diimino)bis [2,4,6-triiodo-3-(acetylamino)methyl-benzoic acid], 5,5'-(apidoldiimino)bis(2,4,6-triiodo-N-methyl-isophthalamic acid), 5,5'-(sebacoyl-diimino)-bis(2,4,6-triiodo-N-methylisophthalamic acid), 5,5-[N,N-diacetyl-(4,9-dioxy-2,11-dihydroxy-1,12-dodecanediyl)diimino]bis(2,4,6-triiodo-N-methyl-isophthalmic acid, 5,5', 5"-nitrilotriacetyltriimino) tris(2,4,6-triiodo-N-methyl-isophthalamic acid), 4-hydroxy-3,5-diiodo-alpha-phenylbenzenepropanoic acid, 3,5-diiodo-4-oxo-1(4H)-pyridine acetic acid, 1,4-dihydro-3,5-diiodo-1-methyl-4-oxo -2,6-pyridinedicarboxylic acid, 5-iodo-2-oxo-1(2H)-pyridine acetic acid, and N-(2-hydroxyethyl)-2,4,6-triiodo-5-[2-[2,4,6-triiodo-3-(N-methylacetamido)-5-(methylcarbomoyl)benzamino]acetamido]-isophthalamic acid, as well as other non-ionic X-ray contrast agents proposed in the literature e.g. in J. Am. Pharm. Assoc., Sci Ed. 42: 721 (1953), CH-A-480071, JACS 78: 3210 (1956), DE-A-2229360, U.S. Pat. No. 3,476,802, Arch. Pharm. (Weinheim, Ger) 306: 11 834 (1973 , J. Med. Chem. 6: 24 (1963), FR-M-6777, Pharmazie 16: 389 (1961), U.S. Pat. Nos. 2,705,726, 2,895,988, Chem. Ber. 93: 2347 (1960), SA-A-68/01614, Acta Radiol. 12: 882 (1972 , GB-A-870321, Rec. Trav. Chim. 87: 308 (1968), East German Patent 67209, DE-A-2050217, DE-A-2405652, Farm Ed. Sci. 28: 912(1973), Farm Ed. Sci. 28: 996 (1973), J. Med. Chem. 9: 964 (1966), Arzheim.-Forsch 14: 451 (1964), SE-A-344166, GB-1346796, U.S. Pat. Nos. 2,551,696, 1,993,039, Ann 494: 284 (1932), J. Pharm. Soc. (Japan) 50: 727 (1930), and U.S. Pat. No. 4,005,188. The disclosures of these and all other documents cited therein are incorporated herein by reference.

Both non-ionic and ionic X-ray contrast agents have their advantages in the MRI contrast media of the invention.

Thus using ionic X-ray contrast agents, a lower concentration can be used to achieve the same osmotic effect. However, non-ionics are especially suitable for contrast media for administration to young children and persons with perfused GI systems or suspected perfusion of the organ because of the generally lower systematic toxicity of non-ionic agents. Another advantage of the non-ionic agents is that they do not precipitate in the stomach.

The X-ray contrast agents are more preferred as osmoactive agents than the conventional osmoactive agents such as the mannitol used in the Schering(EP-A-124766)/Claussen et al. (supra) studies since the side effects, meteorism and diarrhoea, observed with mannitol should be reduced or eliminated.

The concentration of the X-ray contrast agent in the contrast media of the invention may vary over a wide range depending on factors such as its own chemical nature, the chemical and physical nature of the paramagnetic substance and other components in the contrast media, the intended administration route, the pre-administration dilution ratio (where the contrast medium is in a concentrated form for dilution, dissolution or dispersion prior to administration), and machine parameters such as the intended MRI pulse sequence or intended X-ray electron voltage. Conveniently however, the concentration of the X-ray contrast agent is such that the formulation ready for administration contains 2 to 370 mgI/ml, especially 5 to 300 mgI/ml, most especially 10 to 200 mgI/ml.

The dosage of the iodinated X-ray contrast medium will also vary over a wide range, and will be dependent on the same factors as mentioned above. However conveniently a dosage of 10 mgI/kg to 5 gI/kg, especially 100 mgI/kg to 2gI/kg may be given.

The paramagnetic substance in the contrast medium of the invention can be any physiologically tolerable paramagnetic metal species containing substance. Chelates of paramagnetic metal species are particularly preferred, in particular chelates with cyclic or acyclic polyaminocarboxylic acids or derivatives, e.g. amides and esters, thereof. The chelating agents can conveniently be those mentioned in the literature discussed above, although DTPA (see U.S. Pat. No. 4,647,447 (Schering)), DTPA-bismethylamide (see WO86/02841 (Salutar)), DTPA-bis(hydroxylated-alkylamides) (see EP-A-130934 (Schering) and U.S. Pat. No. 4,826,673 (Mallinckrodt)), DOTA (see U.S. Pat. No. 4,639,365 (Sherry)), D03A and Hp-D03A (1,4,7,10-tetraazacyclododecane-1,4,7-triacetic acid and 1,4,7,10-tetraazacyclododecane-1(2-hydroxypropyl)-4,7,10-triacetic acid—see EP-A-232751 (Squibb)), are particularly preferred, especially for chelation of Gd(III). Other suitable paramagnetic metal chelates and chelating agents are disclosed for example in those patent publications and in EP-A-71564, EP-A-165728, EP-A-232751, EP-A-230893, EP-A-292689, EP-A-287465, DE-A-3633245, DE-A-3324235, EP-A-250358, EP-A-263059, EP-A-173163, EP-A-255471, U.S. Pat. Nos. 4,639,365, 4,687,659, WO86/02005, WO87/02893, WO85/05554, WO87/01594, WO87/06229, and in International Patent Applications Nos. PCT/EP90/00078 and PCT/EP90/00079 of Nycomed AS.

The paramagnetic substance can be soluble or insoluble and may, if desired, be bound to a carrier material, e.g. as suggested by Nycomed in EP-A-184899 and EP-A-186947. Where the substance is carrier bound, the carrier material is preferably biotolerable and non-biodegradable and particulary mention in this regard may be made of insoluble polysaccharides and insoluble derivatives thereof, e.g. such as cellulose or those disclosed in EP-A-184899. It is also possible to use soluble salts of physiologically tolerable paramagnetic metals or particles of insoluble paramagnetic compounds, such as the gadolinium oxalate suggested by Runge in U.S. Pat. No. 4,615,879.

In the paramagnetic substance, the paramagnetic metal is conveniently a metal having an atomic number of 21–29, 42, 44 and 57–71, e.g. gadolinium, europium, dysprosium, holmium, erbium, manganese, iron, chromium, nickel and copper. Gd, Dy, Mn, Cr and Fe are particularly preferred.

Where the paramagnetic metal is bound in a chelate complex, to reduce liberation in vivo of the paramagnetic metal it may be advantageous to include a buffer and/or an excess of the chelating agent, or a weaker metal complex thereof, e.g. as suggested in EP-A-270483.

The concentration and dosage of the paramagnetic substance will depend on factors such as those mentioned above in connection with the concentration and dosage of the X-ray contrast agent. In general, however, the concentration will be such that the contrast medium in a form ready for administration will contain the paramagnetic metal (PM) at 0.01 mmol to 1 mol PM/l, e.g. 0.01 to 100 mmol PM/l, especially 0.1 to 50 mmol PM/l particularly 0.1 to 10 mmol PM/l. Similarly, the dosage will conveniently lie in the range 0.01 micromol PM/kg to 10 mmol PM/kg, especially 0.1 micromol PM/kg to 5 mmol PM/kg, particularly 1 micromol PM/kg to 1 mmol PM/kg bodyweight.

The contrast media of the invention may, of course, contain other components than the paramagnetic substance and the X-ray contrast agent, for example conventional pharmaceutical or veterinary formulation aids such as wetting agents, disintegrants, binders, fillers, stabilizers, viscosity enhancing agents, flavoring agents, coloring agents, buffers, pH adjusting agents, and liquid carrier media.

The inclusion of buffers in the contrast media of the invention is particularly preferred.

To improve contact at the gut wall, especially where the paramagnetic substance is particulate, it may also be advantageous to incorporate into the contrast medium of the invention a mucoadhesive, for example, a polyacrylic acid or a derivative thereof, xanthan gum etc.

The contrast media of the invention, if necessary after dilution with or dispersion or dissolution in aqueous media, are particularly suited for use in the diagnostic imaging by MRI and/or X-ray imaging of the GI tract, and in particular the duodenum and the intestines. For such a purpose the contrast medium may be administered orally or rectally or through orally or rectally inserted tubes. However, as indicated earlier, the media are of course suitable for use in imaging other externally voided body cavities, e.g. the bladder, uterus and vagina.

Thus viewed from another aspect, the invention provides the use of an iodinated X-ray contrast agent for the manufacture of a contrast medium further comprising a paramagnetic metal species, said medium being for use in diagnostic imaging of the gastrointestinal tract.

Viewed from a further aspect, the invention provides the use of a physiologically tolerable paramagnetic metal species containing substance for the manufacture of a contrast medium further comprising an iodinated X-ray contrast agent, said medium being for use in diagnostic imaging of the gastrointestinal tract.

Viewed from yet a further aspect, the invention provides a method of generating an image of a human or non-human, e.g. mammalian, subject, said method comprising administering a contrast medium according to the invention into an externally voided body cavity, e.g. the gastrointestinal tract, and generating an X-ray and/or magnetic resonance image of at least part said cavity.

Viewed from a still yet further aspect the invention provides a diagnostic contrast agent kit comprising a physiologically tolerable paramagnetic species containing substance and, packaged separately thereto, a water soluble iodinated X-ray contrast agent.

In the method of the invention, the contrast medium will generally be administered in a dose of at least 30 ml for an adult human subject, more usually 200 to 1500 ml, especially 300 to 1000 ml. The dose may be taken in portions, e.g. for oral administration about ⅔ being ingested 20 minutes before imaging and the remainder being ingested immediately before the subject is placed in the imager.

The invention is further illustrated by the following non-limiting examples:

EXAMPLE 1

Solution for Oral Administration

| | |
|---|---|
| GdDTPA-bismethylamide trihydrate (GdDTPA-BMA) | 627 mg |
| Iohexol | 302 g |
| Saccharin sodium | 1 g |
| Ethanol | 10 g |
| Orange essence | 0.8 g |
| Water | ad 1000 ml |

GdDTPA-BAM, saccharin sodium and iohexol were dissolved in water (500 ml). Orange essence was dissolved in ethanol and slowly added to the aqueous solution. Water was added to bring the volume to 1000 ml and the solution was filled into a 1000 ml vial. The solution contains 1 mmol gadolinium and 140 g I per liter.

GdDTPA-BAM and iohexol were prepared according to the methods of U.S. Pat. Nos. 4,687,659 (Salutar) and 4,250,113 (Nycomed) respectively.

EXAMPLE 2

Solution for Oral Administration

| Gadolinium-DTPA-dimeglumine | 9.83 g |
|---|---|
| Metrizoate meglumine | 422 g |
| Saccharin sodium | 8.5 g |
| Polysorbate 80 | 5.0 g |
| Aniseed oil | 0.5 g |
| Water | ad 1000 ml |

The components were dissolved in water (500 ml) at 50° C. Water was added to bring the volume to 1000 ml and the solution was filled into a 1000 ml vial. The solution contained 10 mmol Gd and 200 g i per liter.

GdDTPA-dimeglumine and metrizoate were prepared according to the methods of U.S. Pat. Nos. 4,647,447 (Schering) and 3,476,802 (Nycomed) respectively.

EXAMPLE 3

Concentrate for Dilution before Oral or Rectal Administration 627 mg (10 mmol) GdDTPA-BMA (See Example 1) is dissolved in 100 ml Gastrografin ® (available from Schering AG).

Gastrografin contains the X-ray contrast agent diatrizoate sodium and diatrizoate meglumine at a concentration of 370 mg I/ml.

The concentrate is diluted with three times its volume of water or juice before administration.

EXAMPLE 4

Solution for Oral/Rectal Administration 2 ml Magnevist ® (available from Schering AG) is mixed into 100 ml Gastrografin ® (see Example 3) and the mixture is diluted with 898 ml water. The resulting solution contains 1 mmol Gd/l and 37 gI/l.

EXAMPLE 5

Solution for Oral Administration

| GdDOTA lysine salt | 14.3 g |
|---|---|
| Iopamidol | 408 g |
| Water | ad 1000 ml |

The components were dissolved in water (500 ml) at 40° C. Water was added to bring the volume to 1000 ml and the solution was filled into a 1000 ml vial. The solution contained 20 mmol gadolinium and 200 g I per liter.

GdDOTA lysine salt and Iopamidol were prepared according to the methods of WO87/06229 (Guerbet) and U.S. Pat. No. 4,001,323 (Bracco) respectively.

I claim:

1. An enteral contrast medium for X-ray and MRI diagnostic imaging of a human or animal externally voided body cavity comprising a diagnostically effective amount of a physiologically tolerable paramagnetic metal species containing substance together with a sufficient amount of a water soluble iodinated X-ray contrast agent to enhance MRI imaging of said externally voided body cavity; wherein said paramagnetic metal species containing substance and said iodinated X-ray contrast agent are not the same molecule.

2. A contrast medium as claimed in claim 1, wherein said X-ray contrast agent is selected from iodamide, iothalamate, diatrizoate, ioxaglate and metrizoate salts and metrizamide, iopamidol, iohexol, iotrolan, iodecimol, iodixanol, ioglucol, ioglucomide, ioglunioe, iogulamide, iomeprol, iopentol, iopromide, iosarcol, iosimide, iotasul, iovasol and ioxilan.

3. A contrast medium as claimed in claim 1 wherein said X-ray contrast agent is present at a concentration such that the formulation ready for administration contains 2 to 370 mg I/ml.

4. A contrast medium as claimed in claim 1 wherein said physiologically tolerable paramagnetic metal species containing substance comprises a chelate of a paramagnetic metal ion.

5. A contrast medium as claimed in claim 4, wherein the chelant for said chelate comprises a polyaminocarboxylic acid or a derivative thereof.

6. A contrast medium as claimed in claim 1 wherein said paramagnetic metal species containing substance incorporates a carrier material.

7. A contrast medium as claimed in claim 6, wherein said carrier material is an insoluble polysaccharide or an insoluble derivative thereof.

8. A contrast medium as claimed in claim 1 wherein said paramagnetic metal has an atomic number of 21-29, 42, 44 or 55-71.

9. A contrast medium as claimed in claim 1 wherein said paramagnetic metal is selected from Gd, Dy, Mn, Cr and Fe.

10. A contract medium as claimed in claim 1 wherein said paramagnetic metal is present at a concentration such that the formulation ready for administration contains 0.01 mmol to 1 mol paramagnetic metal per liter.

11. A method of generating an image of a human or non-human body, said method comprising administering to an externally voided body cavity of said body a diagnostically effective amount of a contrast medium as claimed in claim 1 and generating an X-ray or magnetic resonance image of at least part of said body.

12. A contract medium as claimed in claim 2 wherein said X-ray contrast agent is present at a concentration such that the formulation ready for administration contains 2 to 370 mg I/ml.

13. A contrast medium as claimed in claim 2 wherein said physiologically tolerable paramagnetic metal species containing substance comprises a chelate of a paramagnetic metal ion.

14. A contrast medium as claimed in claim 3 wherein said physiologically tolerable paramagnetic metal species containing substance comprises a chelate of a paramagnetic metal ion.

15. A contrast medium as claimed in claim 2 wherein said paramagnetic metal is selected from Gd, Dy, Mn, Cr and Fe.

16. A contrast medium as claimed in claim 3 wherein said paramagnetic metal is selected from Gd, Dy, Mn, Cr and Fe.

17. A contrast medium as claimed in claim 12, wherein said paramagnetic metal is present at a concentration such that the formulation ready for administration contains 0.01 mmol to 1 mol paramagnetic metal per liter.

18. A method of generating an image of a human or non-human body, said method comprising administering to an externally voided body cavity of said body a diagnostically effective amount of a contrast medium as claimed in claim 12 and generating an X-ray or magnetic resonance image of at least part of said body.

19. A method of generating an image of a human or non-human body, said method comprising administering to an externally voided body cavity of said body a diagnostically effective amount of a contrast medium as claimed in claim 12 and generating an X-ray or magnetic resonance image of a human GI tract or duodenum.

20. A diagnostic contrast agent kit for X-ray and MRI imaging of a human or animal externally voided body cavity comprising a diagnostically effective amount of a physiologically tolerable paramagnetic metal species containing substance, and packaged separately thereto, a sufficient amount of a water soluable iodinated X-ray contrast agent to enhance MRI imaging of said externally voided body cavity; wherein said paramagnetic metal species containing substance and said iodinated X-ray contrast agent are not the same molecule.

* * * * *